US012575794B2

(12) United States Patent
Gutierrez-Hernandez et al.

(10) Patent No.: US 12,575,794 B2
(45) Date of Patent: Mar. 17, 2026

(54) SYSTEMS AND METHODS FOR WIRELESS NEUROSENSING

(71) Applicants:Melany Gutierrez-Hernandez, Miami, FL (US); Sally P. Duarte, Miami, FL (US); Satheesh Bojja-Venkatakrishnan, Miami, FL (US); Jorge Riera Diaz, Miami, FL (US); John L. Volakis, Miami, FL (US)

(72) Inventors: Melany Gutierrez-Hernandez, Miami, FL (US); Sally P. Duarte, Miami, FL (US); Satheesh Bojja-Venkatakrishnan, Miami, FL (US); Jorge Riera Diaz, Miami, FL (US); John L. Volakis, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 19/185,873

(22) Filed: Apr. 22, 2025

(65) Prior Publication Data
US 2025/0359825 A1 Nov. 27, 2025

Related U.S. Application Data

(60) Provisional application No. 63/650,572, filed on May 22, 2024.

(51) Int. Cl.
*A61B 5/00* (2006.01)
*A61B 5/25* (2021.01)

(52) U.S. Cl.
CPC .............. *A61B 5/7228* (2013.01); *A61B 5/25* (2021.01); *A61B 5/6847* (2013.01); *A61B 5/6878* (2013.01); *A61B 2560/0468* (2013.01)

(58) Field of Classification Search
CPC ..................................................... A61B 5/7228
See application file for complete search history.

(56) References Cited

U.S. PATENT DOCUMENTS

| | | | |
|---|---|---|---|
| 11,412,989 B2 * | 8/2022 | Wijshoff .............. | A61B 5/0295 |
| 2009/0143696 A1 * | 6/2009 | Najafi .................. | A61B 5/6864 |
| | | | 600/561 |
| 2013/0085350 A1 * | 4/2013 | Schugt ................. | A61B 5/0031 |
| | | | 607/59 |

OTHER PUBLICATIONS

Gutierrez-Hernandez, Melany, et al. "Battery-less, Multichannel and Wireless Recorder for Neuronal Activity Monitoring." 2024 International Applied Computational Electromagnetics Society Symposium (ACES). IEEE, 2024.

* cited by examiner

*Primary Examiner* — Joseph M Santos Rodriguez
(74) *Attorney, Agent, or Firm* — SALIWANCHIK, LLOYD & EISENSCHENK

(57) ABSTRACT
Systems and methods for neurosensing are provided. A wireless neurosensing system (WiNS), which can be battery-less and/or multichannel, can include a sensor that receives an external electromagnetic (EM) signal (i.e., a carrier signal) through biological tissue communication. The sensor can be configured to be implanted into a subject (e.g., an organoid or a mammalian subject, such as a human subject) and can be referred to herein as the implant. The external EM signal can be received from an interrogator configured to remain outside the subject. The sensor can mix the carrier signal with an electrical signal of interest (SoI) and transmit it back to the external interrogator for posterior demodulation and/or processing. The systems and methods can be employed in many applications to measure the electrical signal in biological or non-biological settings.

20 Claims, 14 Drawing Sheets

Implant          Interrogator

Implant                 Interrogator

| Frequency | Proposed | Ref. [2] | Ref. [3] | Ref. [4] |
|-----------|----------|----------|----------|----------|
| 2.4 GHz   | -4.3 dB  | -16 dB   | -7 dB    | -9 dB    |
| 4.8 GHz   | -8.7 dB  | -13 dB   | -15 dB   | -13 dB   |

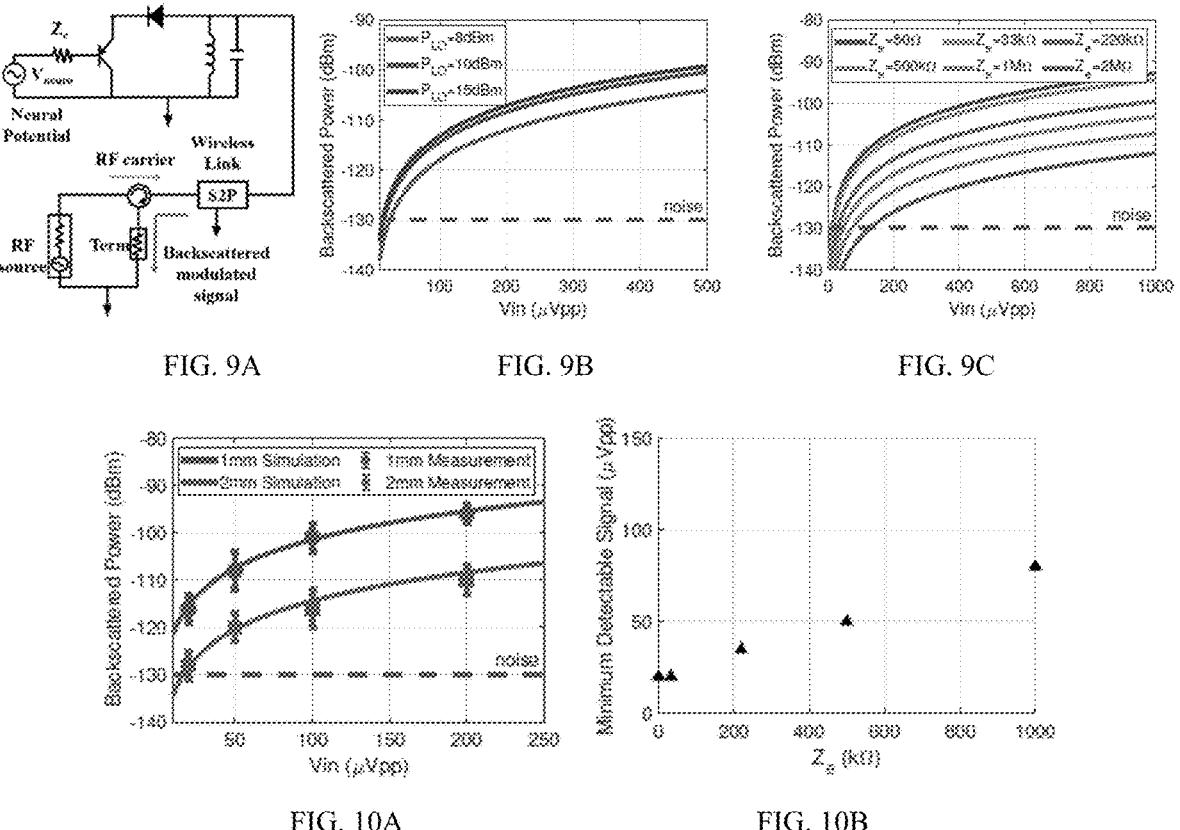
FIG. 9A                    FIG. 9B                    FIG. 9C
FIG. 10A                    FIG. 10B

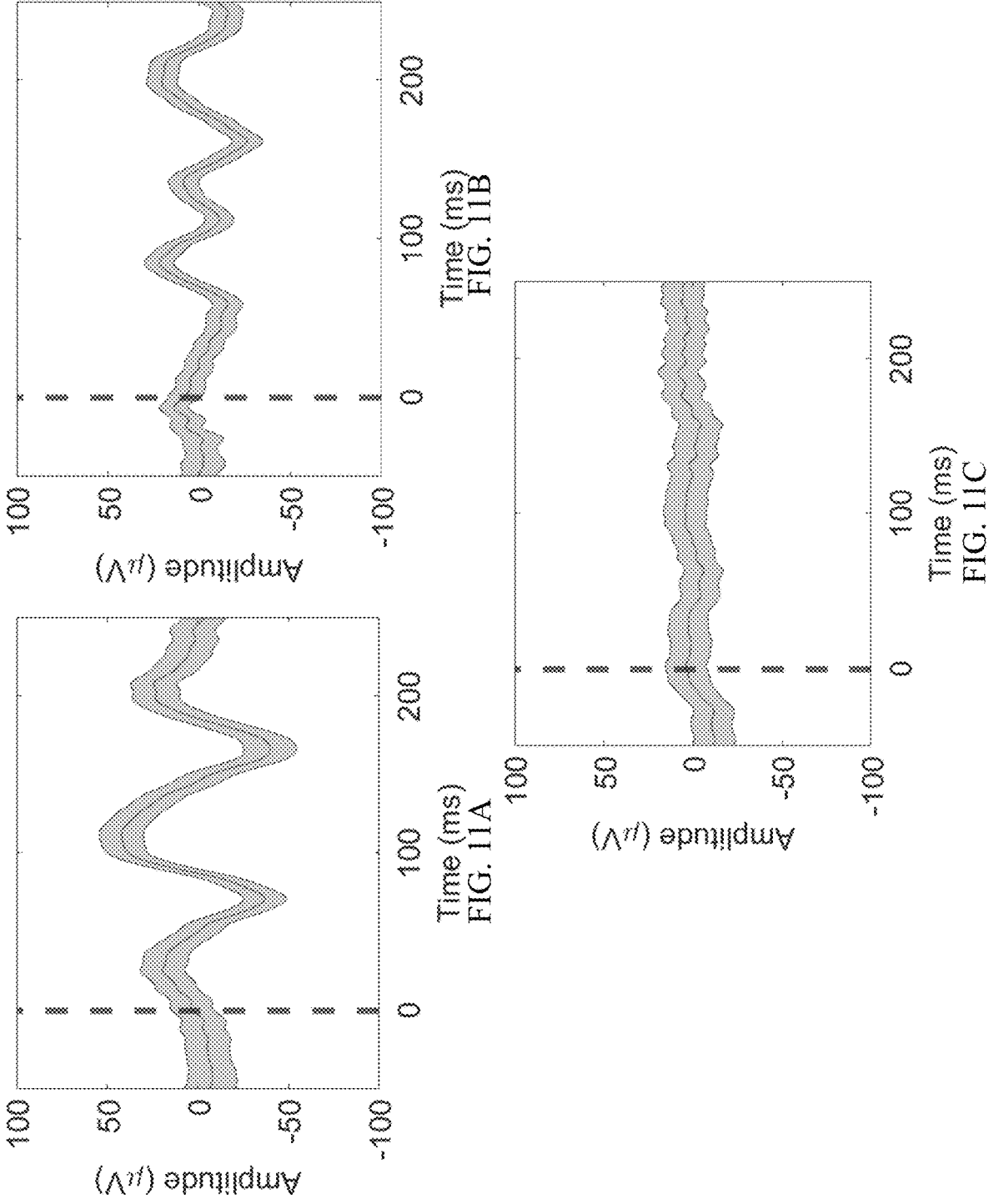

| Parameters | Size ($mm^3$) | Weight (g) | Number of channels | Power Con. ($mW$) | MDS ($\mu V_{pp}$) | Communicat. dist. ($mm$) | Experimental Validation |
|---|---|---|---|---|---|---|---|
| Borton et. al [22] | 56 × 42 × 9 | 44.5 | 100 | 90.6 | 24.3 | 1000 – 3000 | *in-vivo, fully implanted* |
| Muller et. al [7] | 6.5 × 6.5 $mm^2$ | | 64 | 0.225 | 3.53 | 12.5 | *in-vivo* |
| Lee et. al [23] | 19 × 19 × 30 | 5.7 | 32 | 35 | 8.5 | | *in-vivo, no fully implanted* |
| Seo et. al [24] | 3 × 1 × 0.8 | | 1 | 0 | 500 | 8.8 | *in-vivo, fully implanted* |
| Liu et. al [25] | 9 × 8 × 0.3 | 0.054 | 1 | 0 | 60 | 15 – 21 | *in-vivo, fully implanted* |
| Chen et. al [13] | 88 × 58 × 0.8 | | 1 | 0 | 200 | 2 | benchtop |
| Moncion et. al [11] | 40 × 40 $mm^2$ | | 8 | 0.008 | 15 (averaged potential) | 2 | *in-vivo, no fully implanted* |
| This study | 45 × 29 × 1.6 | 5 | 1 | 0 | 20 | 2 | *in-vivo, fully implanted* |

FIG. 12

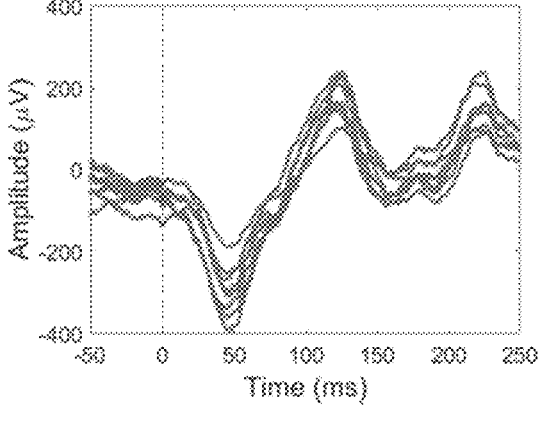
FIG. 13A
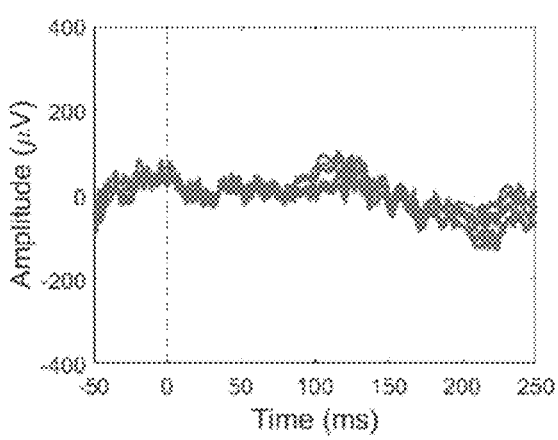
FIG. 13B
|  | This work | Ref. [5] | Ref. [6] |
|---|---|---|---|
| Size | 45x30x3 mm³ | 59x38x15 mm³ | 19x19x30 mm³ |
| Weight | 5 g | 56 g | 5.7 g |
| No. channel | 8 | 4 | 32 |
| Power source | RF (2.4 GHz) & PV cell | Battery (90 days life) | Inductive (13.56MHz) |
| Power Cons. | 98 µW |  | 35mW |
FIG. 14

SYSTEMS AND METHODS FOR WIRELESS NEUROSENSING

CROSS-REFERENCE TO RELATED APPLICATION

This application claims the benefit of U.S. Provisional Application Ser. No. 63/650,572, filed May 22, 2024, the disclosure of which is hereby incorporated by reference in its entirety, including all figures, tables, and drawings.

GOVERNMENT SUPPORT CLAUSE

This invention was made with government support under 2052764 awarded by the National Science Foundation. The government has certain rights in the invention.

BACKGROUND

In 2015, 1.2% of the total United States population had active epilepsy. Epilepsy can be caused by different conditions that affect a person's brain, such as stroke, brain tumor, or traumatic brain injury, though more often the cause is unknown. Neural recordings can provide vital information about brain functionality and are used to detect epileptic activity. Electrocorticogram (ECoG) is a frequently applied technique used to identify the origination of seizures. ECoG recording is the most invasive type of electroencephalographic (EEG) signal acquisition and, usually, involves wires that remain protruding from the skull. This exposes the patient to increased risk of infection, hemorrhage, and significant discomfort.

BRIEF SUMMARY

Embodiments of the subject invention provide novel and advantageous systems and methods for neurosensing. A wireless neurosensing system (WiNS), which can be battery-less and/or multichannel, can include a sensor that receives an external electromagnetic (EM) signal (i.e., a carrier signal) through biological tissue communication. The sensor can be configured to be implanted into a subject (e.g., a mammalian subject, such as a human subject) and can be referred to herein as the implant. The external EM signal can be received from an interrogator configured to remain outside the subject. The sensor can mix the carrier signal with an electrical signal of interest (SoI) and transmit it back to the external interrogator for posterior demodulation and/or processing. The systems and methods can be employed in many applications to measure the electrical signal in biological or non-biological settings.

In an embodiment, a system for sensing (e.g., wireless, battery-less, and/or multichannel sensing) signals (e.g., neural, cardiac, and/or electrochemically-based signals) can comprise: an implant configured to be implanted and/or embedded in a subject (e.g., below the skin or in the skull of the subject); and an interrogator configured to communicate with the implant while being external to the subject. The subject can be a mammalian (e.g. human) subject or an organoid. The implant can comprise: at least two electrodes; and a sensor connected (e.g., via wired connection) to the at least two electrodes and comprising a transistor (e.g., a bipolar junction transistor (BJT)), a diode (e.g., a Schottky diode), and a first antenna (e.g., a near-field communication (NFC) antenna and/or a radio frequency (RF) antenna) configured to communicate with the interrogator while the implant is implanted/embedded in the subject. The interrogator can comprise a second antenna (e.g., an NFC antenna and/or an RF antenna) configured to communicate with the first antenna while the implant is implanted/embedded in the subject and the interrogator is external to the subject. The interrogator can be configured to generate a carrier signal, transmit the carrier signal to the implant, and receive a modulated signal from the implant. The implant can be configured to receive the carrier signal from the interrogator, mix the carrier signal with a SoI (e.g., neural signals, cardiac signals, electrochemically-based signals such as those coming from a stent and the sensor in combination) from the subject to generate the modulated signal, and backscatter the modulated signal to the interrogator. The system can be configured such that the implant and the interrogator are not connected to each other by any wire (i.e., the system can be configured such that the implant and the interrogator communicate with each other only wirelessly while the implant is implanted/embedded in the subject and the interrogator is external to the subject). The system can further comprise a demodulation circuit connected (e.g., via wired connection) to the interrogator and configured to demodulate the modulated signal. The implant can be coated with a biocompatible material (e.g., polydimethylsiloxane (PDMS)). The first antenna can comprise a shorting pin, and/or the second antenna can comprise a shorting pin. The implant can further comprise a passive impedance matching (PIM) network. The implant can further comprise a photovoltaic (PV) cell and at least one photodiode (PD) (e.g., three PDs or at least three PDs). The interrogator can further comprise a first light source configured to communication with the PV cell of the implant and at least one second light source (e.g., three second light sources or at least three second light sources) configured to respectively communicate with the at least one PD of the implant. The light sources can be activated by a microcontroller for automatic control. The system can be used to implement closed-loop feedback combining multielectrode arrays and new antennas for on-site computing using multi-domain organoids. The system can further comprise at least one conductive stent configured to act as at least one conformal antenna, respectively, to communicate amperometric-based biological signals from vessels of the subject.

In another embodiment, a method for sensing (e.g., wireless, battery-less, and/or multichannel sensing) signals (e.g., neural, cardiac, and/or electrochemically-based signals) can comprise: implanting an implant in a subject (e.g., below the skin or in the skull of the subject); generating, with an interrogator that is external to the subject, a carrier signal; transmitting, by the interrogator, the carrier signal from the interrogator to the implant; receiving, by the implant, the carrier signal from the interrogator; mixing, by the implant, the carrier signal with a SoI (e.g., neural signals, cardiac signals, electrochemically-based signals such as those coming from a stent and the sensor in combination) from the subject to generate a modulated signal; backscattering, by the implant, the modulated signal to the interrogator; and receiving, by the interrogator, the modulated signal from the implant. The subject can be a mammalian (e.g. human) subject or an organoid. The implant can comprise: at least two electrodes; and a sensor connected (e.g., via wired connection) to the at least two electrodes and comprising a transistor (e.g., a BJT), a diode (e.g., a Schottky diode), and a first antenna (e.g., an NFC antenna and/or an RF antenna) configured to communicate with the interrogator while the implant is implanted/embedded in the subject. The interrogator can comprise a second antenna (e.g., an NFC antenna and/or an RF antenna) configured to communicate with the first antenna while the implant is implanted/embedded in the subject and the interrogator is external to the subject. The implant and the interrogator can be configured such that the implant and the interrogator are not connected to each other by any wire (i.e., the implant and the interrogator communicate with each other only wirelessly while the implant is implanted/embedded in the subject and the interrogator is external to the subject). The method can further comprise demodulating the modulated signal using a demodulation circuit connected (e.g., via wired connection) to the interrogator. The method can further comprise, before implanting the implant into the skull of the subject, coating the implant with a biocompatible material (e.g., PDMS). The first antenna can comprise a shorting pin, and/or the second antenna can comprise a shorting pin. The implant can further comprise a PIM network. The implant can further comprise a PV cell and at least one PD (e.g., three PDs or at least three PDs). The interrogator can further comprise a first light source configured to communication with the PV cell of the implant and at least one second light source (e.g., three second light sources or at least three second light sources) configured to respectively communicate with the at least one PD of the implant. The method can further comprise: communicating, by the first light source, with the PV cell of the implant; and/or using the at least one second light source to respectively trigger the at least one PD of the implant. The light sources can be activated by a microcontroller for automatic control. The method can further comprise implementing closed-loop feedback combining multielectrode arrays and new antennas for on-site computing using multidomain organoids. The method can further comprise communicating (by at least one conductive stent configured to act as at least one conformal antenna, respectively) amperometric-based biological signals from vessels of the subject.

BRIEF DESCRIPTION OF DRAWINGS

FIG. 9A shows a simplified ADS (advanced design system) circuit model with a two-port S-parameter network representing a wireless link between an implanted recorder and an external antenna. The S-parameters were extracted from HFSS simulations. Additionally, ADS harmonic balance simulator was used to calculate backscattered power.

FIG. 9B shows a plot of backscattered power (in decibels (in reference to milliwatts) (dBm)) versus voltage in (Vin, in microvolts peak to peak ($\mu$Vpp)). This shows backscattered power for three different input RF power ($P_{LO}$) levels as a function of neuropotential amplitude (Ze=33 kiloOhms (kΩ)). The (purple) curve with the highest backscattered power value at Vin=300 μVpp is for $P_{LO}$=15 dBm; the (red) curve with the second-highest backscattered power value at Vin=300 μVpp is for $P_{LO}$=10 dBm; and the (blue) curve with the lowest backscattered power value at Vin=300 μVpp is for $P_{LO}$=5 dBm. The (gray) dashed line shows the noise level of −130 dBm.

FIG. 9C shows a plot of backscattered power (in dBm) versus voltage in (Vin, in μVpp). This shows backscattered power for six different electrode impedances (Ze) as a function of neuropotential amplitude. The (red) curve with the highest backscattered power value at Vin=600 μVpp is for Ze=50 Ohms (Ω); the (teal) curve with the second-highest backscattered power value at Vin=600 μVpp is for Ze=33 kΩ; the (purple) curve with the third-highest back-scattered power value at Vin=600 μVpp is for Ze=220 kΩ; the (pink) curve with the fourth-highest backscattered power value at Vin=600 μVpp is for Ze=500 kΩ; the (light blue) curve with the second-lowest backscattered power value at Vin=600 μVpp is for Ze=1 megaOhm (MΩ); and the (dark blue) curve with the lowest backscattered power value at Vin=600 μVpp is for Ze=2 MΩ. The (gray) dashed line shows the noise level of −130 dBm.

FIG. 10A shows a plot of backscattered power (in dBm) versus voltage in (Vin, in μVpp). This shows backscattered power for as a function of the neuropotential amplitude for two different skin sizes (Ze=33 kΩ). The (red) curve with the higher backscattered power values is for 1 mm simulation; the circular data points are for 1 mm measurement; the (blue) curve with the lower backscattered power values is for 2 mm simulation; and the square data points are for 2 mm measurement. The (gray) dashed line shows the noise level of −130 dBm.

FIG. 10B shows a plot of measured minimum detectable signal (in μVpp) of the wireless recorder as a function of the electrode impedance (Ze, in kΩ). The emulated neural potential was a 1 kHz sinusoidal signal.

FIG. 11A shows a plot of amplitude (in μV) versus time (in ms), showing evoked potential as recorded from a single channel implant in response to hind limb contra lateral stimulation (the vertical (gray) dashed line). Notable responses were observed at approximately 50 and 150 ms as compared to no response without stimulation (control signal).

FIG. 11B shows a plot of amplitude (in μV) versus time (in ms), showing evoked potential recorded from a 1-channel implant in response to hind limb ipsilateral stimulation (the vertical (gray) dashed line).

FIG. 11C shows a plot of amplitude (in μV) versus time (in ms), showing a control signal (no stimulation).

FIG. 12 shows a table of characteristics of a system according to an embodiment of the subject invention compared with related art systems. The bottom row labeled "This study" is for an embodiment of the subject invention. The other rows are for Borton et al. (An implantable wireless neural interface for recording cortical circuit dynamics in moving primates, Journal of Neural Engineering, 10(2): 026010, 2013), Muller et al. (A minimally invasive 64-channel wireless μecog implant, IEEE Journal of Solid-State Circuits, 50:344-359, 2015), Lee et al. (An inductively powered scalable 32-channel wireless neural recording system-on-a-chip for neuroscience applications, IEEE Transactions on Biomedical Circuits and Systems, 4:360-371, 2010), Seo et al. (Wireless recording in the peripheral nervous system with ultrasonic neural dust, Neuron, 91(3): 529-539, 2016), Liu et al. (Fully passive flexible wireless neural recorder for the acquisition of neuropotentials from a rat model, ACS Sensors, 4(12):3175-3185, 2019), Chen et al. (Passive impedance matching for implanted brain-electrode interfaces, IEEE Journal of Electromagnetics, RF and Microwaves in Medicine and Biology, 3(4):233-239, 2019), and Moncion et al. (Multichannel wireless neurosensing system for battery-free monitoring of neuronal activity, Biosensors and Bioelectronics, 213:114455, 2022). All seven of the references mentioned in the previous sentence are hereby incorporated by reference herein in their entireties. The numbers after the "et al." in the left-most column of each row of the table in FIG. 12 can be ignored.

FIG. 13A shows a plot of amplitude (in μV) versus time (in ms), showing evoked potential from an 8-channel recording in response to hind limb stimulation (the vertical (gray) dashed line). There were notable responses at approximately 50 ms and approximately 150 ms.

FIG. 13B shows a plot of amplitude (in μV) versus time (in ms), showing evoked potential from an 8-channel recording with no stimulation (control signal).

FIG. 14 shows a table comparing a system according to an embodiment of the subject invention with related art systems. The column labeled "This work" is for a system according to an embodiment of the subject invention. The column labeled "Ref. [5]" is for a system as disclosed in Martinez-Ramirez et al. (Robust, long-term video EEG monitoring in a porcine model of post-traumatic epilepsy, eNeuro. 2022, 9(4):ENEURO.0025-22.2022, doi: 10.1523/ENEURO.0025-22.2022; which is hereby incorporated by reference herein in its entirety). The column labeled "Ref. [6]" is for a system as disclosed in Lee et. al. (An Inductively-Powered Wireless Neural Recording and Stimulation System for Freely-Behaving Animals, IEEE Trans Biomed Circuits Syst. 2019, 13(2):413-424, doi: 10.1109/TB-CAS.2019.2891303; which is hereby incorporated by reference herein in its entirety).

DETAILED DESCRIPTION

Figure 1A:
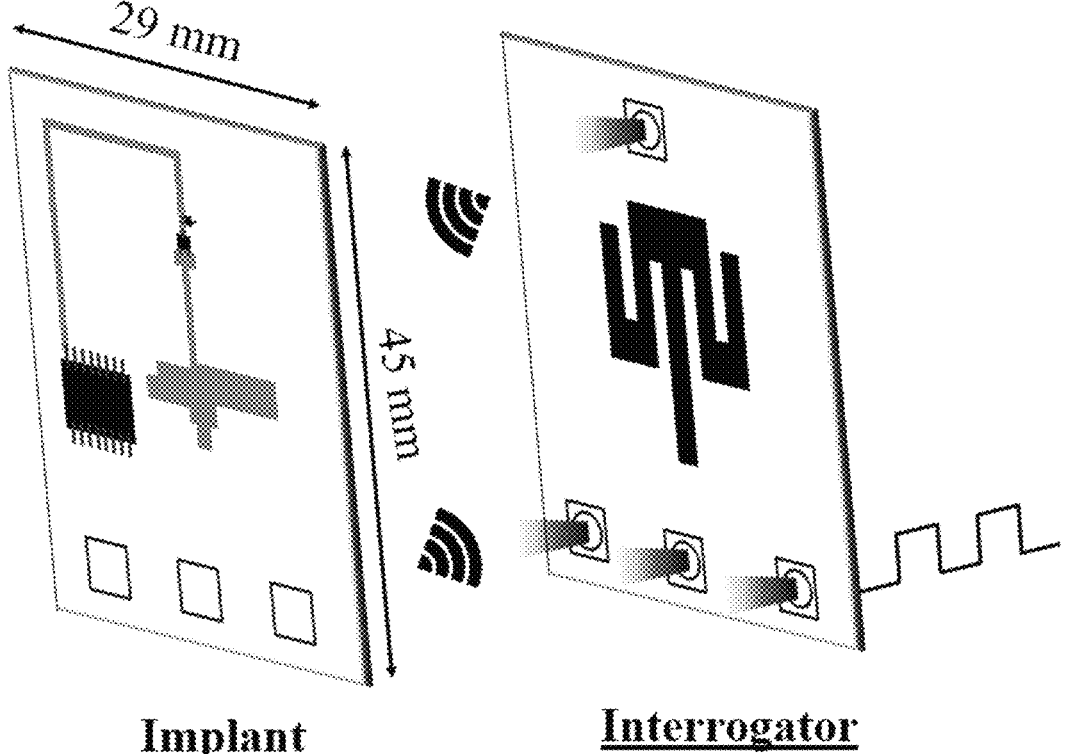
FIG. 1A shows a battery-less, wireless, multichannel implantable sensor, according to an embodiment of the subject invention.

Embodiments of the subject invention provide novel and advantageous systems and methods for neurosensing. A wireless neurosensing system (WiNS), which can be battery-less and/or multichannel, can include a sensor that receives an external electromagnetic (EM) signal (i.e., a carrier signal) through biological tissue communication. The sensor can be configured to be implanted into a subject (e.g., a mammalian subject, such as a human subject) and can be referred to herein as the implant. The external EM signal can be received from an interrogator configured to remain outside the subject. The sensor can mix the carrier signal with an electrical signal of interest (SoI) and transmit it back to the external interrogator for posterior demodulation and/or processing. The systems and methods can be employed in many applications to measure the electrical signal in biological or non-biological settings.

Embodiments can be applied to amperometric/electro-chemical-based monitoring of biological tissues. For example, the system can be used to detect and/or monitor neurological and/or cardiac diseases (e.g., combined with a stent). Also, the WiNS can be integrated with any implant-able sensor and can transmit information on glucose, heart rate, oxygen, uric acid, and other parameters of the subject using a battery-less and wireless methodology.

Implantable sensors offer continuous, real-time monitor-ing of vital health parameters directly from within the body. These sensors enable early detection of diseases and per-sonalized treatment strategies. Radiofrequency (RF) tech-nology plays a crucial role in implantable sensors by facili-tating wireless communication and by providing remote charging to enable battery-less operation. This capability allows for continuous data transmission between the implanted sensor and external monitoring devices. However, when RF transmission is used in dissipative media, such as tissue, RF power can decrease significantly. In addition, many implantable systems rely on a battery that increases the temperature, which can cause tissue damage to the subject. In order to address these issues, embodiments of the subject invention provide an implantable device for record-ing neural activation in a wireless fully passive manner. Related art recorders are of low efficiency and large size due to the separation between antennas and impedance matching circuits. Therefore, a need exists for a new technology that uses RF more efficiently and in a safe manner while requir-ing for a miniature structure to monitor signals of interest.

The WiNS of embodiments of the subject invention can comprise two principal components—the implant and the interrogator. These are depicted in FIGS. 1A-1D. Though certain dimensions are listed in FIG. 1A, these are for exemplary purposes only and should not be construed as limiting. FIG. 1B shows a schematic of the system with the sensor implanted in the scalp of a subject, and FIGS. 1C and 1D show block diagrams of the system.

The operation of the WiNS can rely on wireless commu-nication, such as RF and/or optical communications. The implant and interrogator can be designed with well-matched dual-band antennas for near-field communication (NFC) through skin (e.g., through human skin). Biocompatibility can be ensured by coating the implant with a thin layer of biocompatible material (e.g., polydimethylsiloxane (PDMS)). The carrier signal can be generated at the inter-rogator and transmitted to the implant. This signal can be mixed with neural signals from the brain of the subject to generate a modulated signal. Subsequently, this modulated signal can be backscattered to the interrogator for demodu-lation, demultiplexing, and/or processing. An important fea-ture of the implantable system is the small antenna to enable the communication link between the sensor and the external interrogator. Each antenna of the system can include a shorting pin to reduce antenna size. The system can also include a diode that has two functions. The diode can rectify the received EM signal to allow proper function of the implant, and mix the SoI with the EM carrier signal. Additionally, the sensor can incorporate a transistor (e.g., a bipolar junction transistor (BJT)) that enables passive impedance matching between the low impedance of the antennas and the high impedances of the electrodes (e.g., commercially available electrodes).

The implant can have a width in a range of, for example, 5 millimeters (mm) to 100 mm (or any value, about any value, or subrange contained therein, such as 29 mm, about 29 mm, or in a range of from 20 mm to 35 mm). The implant can have a height in a range of, for example, 5 mm to 100 mm (or any value, about any value, or subrange contained therein, such as 45 mm, about 45 mm, or in a range of from 35 mm to 55 mm). The implant can have a thickness in a range of, for example, 0.01 mm to 8 mm (or any value, about any value, or subrange contained therein, such as in a range of from 0.1 mm to 2 mm).

The optical components of the WiNS can be used for channel multiplexing in battery-free, multichannel operation of the system. A multiplexer, a photovoltaic (PV) cell, and/or at least one photodiode (PD) (e.g., three PDs or at least 3 PDs) can be incorporated into the implant. Also, the inter-rogator can be equipped with at least two light sources (e.g., light emitting diodes (LEDs); such as four light sources (e.g., LEDs)), with one light source used to communicate with the photovoltaic cell, and the remaining light source(s) employed to trigger the appropriate PD(s) within the implant. The power output of the PV cell can provide a stable source for the multiplexer and for the required poten-tial to reverse bias the PD(s). Notably, the output (code) of the PD(s) can be used for channel selection. The light sources can be activated to power a microcontroller for automatic control. As such, a maximum sampling rate (e.g., 10 kilohertz (kHz), about 10 kHz, or at least 10 kHz per channel) can be achieved. With this sampling rate, it is possible to record both normal and epileptic neural signals generated within the brain.

In an embodiment, a method of fabricating a sensor system can include using three-dimensional (3D)-printing for the implant and/or the interrogator, the 3D printing comprising using at least two layers of a polymer (e.g., two layers of acrylate-based polymer) and at least two layers (e.g., three layers) of a conductive material (e.g., a conduc-tive ink, such as silver conductive ink). The sensor can also be fabricated using a traditional, single or multilayered, printed circuit board (PCB) design.

Implantable devices must ensure protection from harm to the subject caused by electricity. In order to ensure this, simulations were conducted over a skin/tissue thickness of 4 mm, as described in more detail in the examples. The results demonstrated that the implant was in compliance with required minimum standards when the carrier power does not exceed 8 decibels (in reference to milliwatts) (dBm), such that the leakage current is less than 0.1 microamps ($\mu$A).

Embodiments of the subject invention can be applied to any implantable amperometric/electrochemical-based sen-sor in biological or non-biological tissues, including a sensor connected to a stent for monitoring blood pressure and cardiac signals. Embodiments can allow for transmission over different depths of tissue (for example, 0.1 mm-13 mm or more, such as 2 mm-13 mm). Embodiments therefore provide safe, miniature, and efficient techniques for continu-ous health monitoring.

Continuous intracranial monitoring of neural activity can be used to map the seizure onset zone in epilepsy patients. Embodiments of the subject invention provide battery-free and multichannel wireless neurosensing systems and meth-ods. A miniaturized, well-packaged passive multichannel recorder matched to high impedance electrodes (e.g., com-mercial electrodes) can be used. The packaged implant can allow for full implantation in animals (e.g., mammals, such as pigs and humans). The smaller antenna for different skin depth shows improvement over related art antennas. Bench-top measurements indicate correct recovery of the neural signals, demonstrating the implant capabilities for neural epilepsy indicators of the wireless system (see also the examples).

In order to overcome limitations in related art battery-operated wireless recorders and those of integrated circuit (IC)-integrated sensors, embodiments of the subject invention provide the WiNS, which can function similarly to RFID (radio frequency identification). The WiNS can include an implanted neural sensor and an external interrogator. The implant can be linked to the neural probes while the external interrogator is connected to a demodulation circuit that receives the neural signals (see also FIG. 6). An external carrier signal can first be transmitted from the interrogator and received by the implanted recorder. A Schottky diode can be used to passively mix the carrier signal with the neural signals coming from brain probes. The modulated neural signals can then be retransmitted to the interrogator for demodulation.

In order to resolve mismatches between the neural probes and recording circuits, WINS can be enhanced with an impedance matching network (see also e.g.; Moncion et al., supra.; and Chen et al., Passive impedance matching . . . , 2019, supra.). This matching network can include a BJT, which can function as an impedance buffer between the neural probes and the Schottky diode. The aforementioned diode can act as a rectifier and a mixer. The WINS can include the impedance matching network and can achieve a higher sensitivity than expected. Therefore, it is required to design an impedance matched network able to capture low neural signals. Additionally, the most recent design has a large size. This creates challenges for fully implanting the recorder for wireless monitoring in any animal.

In order to address the limitations of related art designs, a miniaturized brain implant was developed with its associated interrogator antenna capable of detecting (and/or configured to detect) neuropotentials as low as 20 microvolts peak to peak ($\mu$Vpp). With the aim of lowering the minimum detectable neuropotential signals, a power budget analysis was performed. To determine the minimum detectable neural signal, the following formula can be used:

$$MDS_{Neuro}[dBm] = MDS_{Rx}[dBm] + L_{sys}[dB] \qquad (1)$$

where $L_{sys}$ is the overall system loss and $MDS_{Rx}$ represents the minimum detectable signal at the interrogator system. It is derived as follows:

$$MDS_{Rx} = 10\log_{10}(kTB_{IF}) + NF_{RX} + SNR \qquad (2)$$

where kT is the thermal noise power in dBm per Hz across the bandwidth $B_{IF}$. Also, $NF_{RX}$ is the receiver noise figure calculated for each of the components at the receiver in FIG. 9 and SNR (dB) is the signal to noise ratio in dB. Typically, SNR>10 dB required to visibly observe the recovered signal in the time-domain. The overall system loss can be calculated from:

$$L_{sys} = L_{prop} + L_{conv} + L_{circuit} + L_{electrode} \qquad (3)$$

where $L_{prop}$ represents the propagation loss between the interrogator and implanted antenna at 4.8 GHz$\pm f_{neuro}$, $L_{conv}$ describes the conversion loss associated with the implanted mixer, $L_{circuit}$ represents the impedance mismatch loss between the antenna and the mixer, and $L_{electrode}$ is the impedance mismatch loss between the recording electrode and the implanted recorder.

In order to enhance the system's sensitivity, it is essential to minimize $L_{sys}$. Therefore, $L_{prop}$, $L_{conv}$, $L_{circuit}$, $L_{electrode}$ must be reduced to the lowest possible level (see also, e.g.; Chen et al., Passive impedance matching . . . , 2019, supra.; and Lee et al., Miniaturized fully passive brain implant for wireless neuropotential acquisition, IEEE Antennas and Wireless Propagation Letters, 16:645-648, 2017; which is hereby incorporated by reference herein in its entirety). Low $L_{prop}$ can be accomplished by optimizing the coupling between the implanted and interrogator antennas. Also, $L_{conv}$ and $L_{circuit}$ can be minimized by using an impedance matching network between the implanted antenna and the Schottky diode. $L_{electrode}$ can be decreased by employing an impedance buffer between the electrodes and the Schottky diode. Each of these parameters can be reduced by employing an optimized circuit design.

Full-wave simulations were conducted using a skin mode to design the antenna and its integrated circuitry (see also, Lee et al., Miniaturized fully passive brain implant . . . , 2017, supra.). An in-house genetic algorithm implemented in MAT-LAB was also employed for the antenna design. The dual-band antennas transmit and receive the signals at 2.4 GHz and 4.8 GHz$\pm f_{neuro}$, with $f_{neuro}$ represents the neural signal frequencies. The second harmonic of the mixing diode at 4.8 GHz is employed for signal transmission. This approach is important for achieving a lower noise floor by effectively separating the transmitted 2.4 GHz from the 4.8 GHz signals.

Figure 7A:
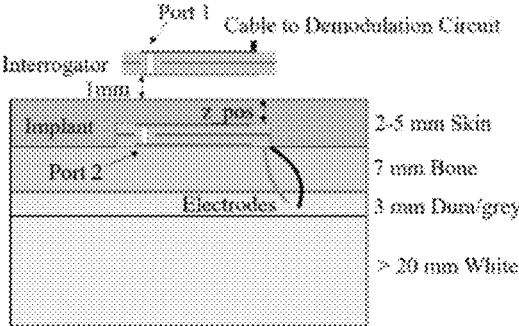
FIG. 7A shows a diagram of a battery-free wireless neural sensor inside a four-layer tissue phantom.

FIG. 7A shows a diagram of the three-dimensional (3D) simulated model, depicting the battery-free wireless sensor inside a tissue-simulating phantom. The phantom model contains four different layers: scalp; skull; dura plus gray matter; and white matter. The electrical characteristics are defined in Kiourti et al. (A wireless fully passive neural recording device for unobtrusive neuropotential monitoring, IEEE Transactions on Biomedical Engineering, 63(1):131-137, 2016; which is hereby incorporated by reference herein in its entirety) and Lee et al. (Miniaturized fully passive brain implant . . . , 2017, supra.). Dura and grey matter can be considered as one layer because of their minimal thickness and their similar electrical properties. Notably, the neural implantable sensor can be placed between the skin and bone to establish the wireless link, and the external dual-band antenna serving as the interrogator can be placed 1 mm above the scalp.

The implanted recorder and external interrogator can be designed and fabricated using a multi-material, multi-layer 3D printing technique to generate the entire circuitry simultaneously. This 3D printed process can include conductive ink (CI) and dielectric ink (DI) as well. The process allowed for 52% smaller footprint as compared to Chen et al. (Passive impedance matching . . . , 2019, supra.). The fabricated implant and interrogator included two layers of acrylate-based polymer ($\epsilon_r$=2.8, tan $\delta$=0.02). Notably, to ensure biocompatibility, the implanted sensor was also coated with polydimethylsiloxane (PDMS) polymer.

Figure 7B:
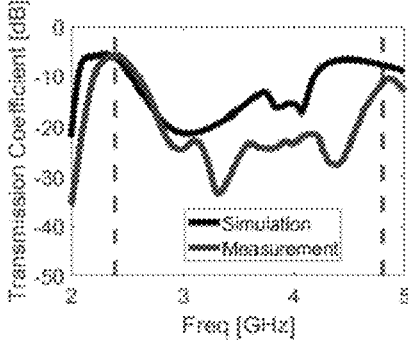
FIG. 7B shows a plot of transmission coefficient (in decibels (dB)) versus frequency (in gigahertz (GHz)), showing simulated and measured transmission coefficient ($S_{21}$) between an implanted antenna and an interrogator antenna with a separation of 2 mm. The (black) curve with the higher transmission coefficient value at 4 GHz is for simulation; and the other (blue) curve is for measurement.
Figures 8A, 8B, 8C, 8D:
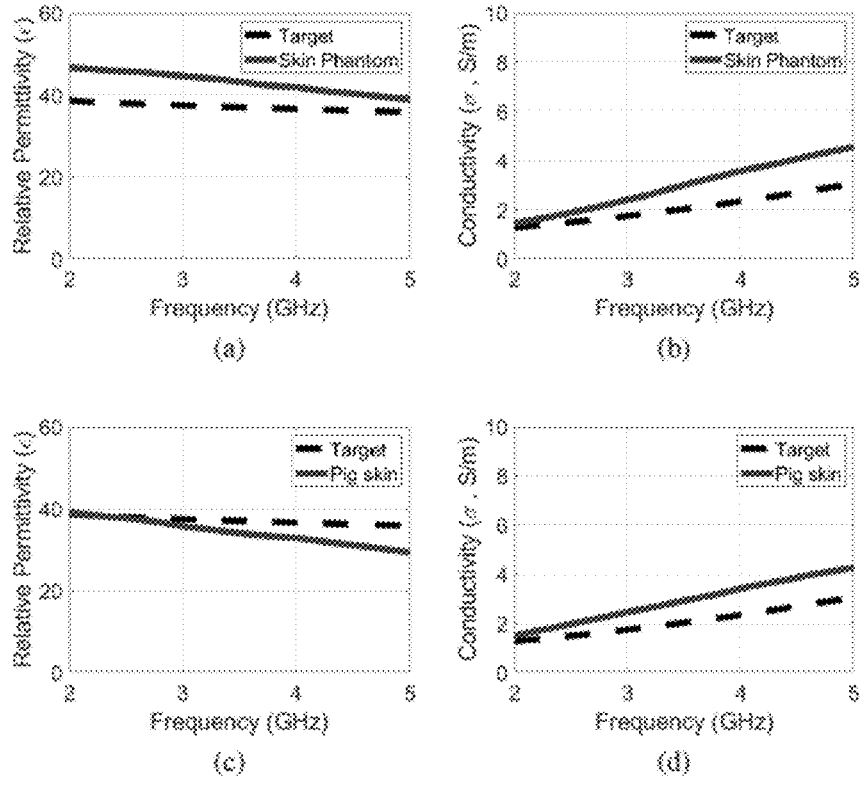
FIG. 8A shows a plot of measured relative permittivity ($\varepsilon$) versus frequency (in GHz). The dotted curve is for target, and the solid curve is for skin phantom.
FIG. 8B shows a plot of measured conductivity ($\sigma$, in Siemens per meter (S/m)) versus frequency (in GHz) (see also, Gabriel et al, The dielectric properties of biological tissues: li. measurements in the frequency range 10 hz to 20 ghz, Physics in Medicine & Biology, 41(11):2251, 1996; which is hereby incorporated by reference herein in its entirety). The dotted curve is for target, and the solid curve is for skin phantom.
FIG. 8C shows a plot of measured relative permittivity ($\varepsilon$) versus frequency (in GHz). The dotted curve is for target, and the solid curve is for pig skin.
FIG. 8D shows a plot of measured conductivity ($\sigma$, in S/m) versus frequency (in GHz) (see also, Gabriel et al., supra.). The dotted curve is for target, and the solid curve is for pig skin.

For validation, FIG. 7B shows the measured and simulated antenna transmission coefficient between implant and interrogator antennas. The implant and interrogator were separated by 2 mm. The plot in FIG. 7B shows good agreement across the frequencies of interest (<3 dB). Importantly, the transmission coefficient is improved over related art designs.

The permittivity and loss tangent of the fabricated skin phantom and pig skin were measured using the Keysight N1501A Dielectric Probe Kit. The measurements were compared to the theoretical skin properties in FIGS. 8A-8D.

The impedance matching circuits (see FIG. 6) were designed and optimized using the Keysight ADS (advanced design system). FIG. 9A shows the simplified ADS model. Using this model, S-parameters from HFSS were incorporated into the ADS circuit model in S2P (see FIG. 9A). A single-tone was used for testing the neuro-potentials signal. However, in practice, neuropotentials occupy multiple frequencies. The power received at the input of the demodulation circuit must be greater than −130 dBm to obtain a minimum detectable signal (MDS) of 20 µVpp. Through electromagnetic cosimulations, WiNS demonstrated effective communication within this range (e.g., the recorder can record signals of 20 µVpp). The backscattered power is shown in FIG. 9B as a function of the neuropotential amplitude for three different RF input ($P_{LO}$) levels. It is demonstrated that the MDS is enhanced when the carrier power increases using an electrode impedance of 33 kΩ. FIG. 9C demonstrates that the system recovers neural signals of less than 100 $\mu V_{pp}$ with an electrode impedance as large as 1 megaOhm (MΩ).

Embodiments of the subject invention can transform the field of neurosensing technology by introducing a revolutionary, fully passive implant. The innovative system operates with safety and discretion, effectively eradicating the risks posed by batteries, harvesters, or regulators that are commonly associated with high power consumption and heat generation around tissue. This innovative approach can advance the field of neurosensing and unlock new possibilities for understanding brain activity. Additionally, the recognition of these neuro potentials can seamlessly extend to any amperometric or electrochemical monitoring of biological tissue. The technology employs RF-backscattering and optical communications through tissues to power the implantable device/system.

The implantable device/system can include a subharmonic mixer, an impedance matching network, an antenna, and a multiplexer accompanied by photodiodes and/or a photovoltaic (PV) cell to power it. On the other hand, the interrogator can include an antenna, photo emitters, and/or a microcontroller to control and power the multiplexer from the exterior (see also FIGS. 1A-1D).

A subharmonic mixer can serve an important function by operating in conjunction with a local oscillator (LO) operating at a frequency that is half that of a conventional mixer's LO frequency. This innovative approach allows the RF signal to be mixed with the second harmonic of the junction's conductance waveform. Unlike a conventional mixer, which requires power at $2f_{LO}$ to generate an output signal of $2f_{LO} \pm f_{neuro}$, a subharmonic mixer only requires $f_{LO}$ to achieve the same output signal $2f_{LO} \pm f_{neuro}$.

In the systems of embodiments of the subject invention, the subharmonic mixer circuit can be an important part of the implanted sensor. It can efficiently generate and transmit the harmonic mixed product to the implanted antenna, enhancing the overall performance of the system. Additionally, it prioritizes safety and ensures that the maximum tissue temperature remains within acceptable levels (e.g., not exceeding 1° C. above normal levels). This combination of efficiency and safety makes the subharmonic mixer an important component.

The circuit can operate using a wireless carrier frequency (e.g., 2.4 GHz) alongside the neural signal frequency, $f_{neuro}$. The finalized subharmonic mixer circuit is designed with precision, incorporating a Schottky diode connected to a set of inductors and capacitors used to achieve matching impedance to the implanted antenna (see FIG. 1A-1D). The Schottky diode can also be used for another function. Specifically, when the interrogator transmits a carrier signal (e.g., a 2.4 GHz carrier signal), the Schottky diode can act as a rectifier, transforming the incoming RF signal into direct current (DC) to self-bias the BJT. Once the BJT is properly biased, the brain signals can be detected and passed through to the BJT. Subsequently, they can be upconverted (e.g., to 4.8 GHZ) by the Schottky diode. In this configuration, the emitter of the BJT can be strategically placed immediately after the Schottky diode. It is necessary to be grounded at the collector. This setup allows the implanted sensor to recognize small signals when the electrode's impedance is still at high levels. That is, the BJT can act as an impedance buffer.

For multichannel operation, the multiplexer can be connected to multiple (e.g., 8) electrodes or channels. These channels can be selected by the photodiodes using an exterior emitter to trigger the channel connection. In addition, an emitting diode can be used to communicate with the photovoltaic cell and provide the required power to operate the multiplexer. As such, a maximum sampling rate (e.g., of 10 kHz or about 10 kHz per channel) can be achieved. With this sampling rate, it is possible to record both normal and epileptic neural signals from the brain.

The implanted and interrogator antennas can be specifically designed to ensure strong EM coupling in the near field. In this context, the radiation pattern of the antenna becomes less significant. Instead, the transmission coefficient ($S_{21}$) emerges as a critical metric for assessing the antenna's transmission properties. Therefore, the objective is to achieve a high transmission coefficient, $S_{21}$, at both 2.4 GHz and 4.8 GHz±$f_{neuro}$, with $f_{neuro}$ representing the neural signal frequencies. The second harmonic of the mixing diode at 4.8 GHz can be employed for signal transmission. This approach is important for achieving a lower noise floor as it operates the transmitted 2.4 GHz from the 4.8 GHz signals. An approximate distance of 1 mm to 5 mm (e.g., 2 mm to 5 mm) between the antennas is typical and accounts for the head skin layer between the implant and the external interrogator.

A high $S_{21}$ at 4.8 GHz minimizes the overall loss of the recorded neural signals, thereby enhancing the system's sensitivity. In addition, a high $S_{21}$ at 2.4 GHz indicates that the minimum carrier signal power needed to turn on the mixer diodes will be low. This aspect is also important for ensuring the patient's safety.

To streamline the integration of the antenna with the implanted circuits, a printed circuit board (PCB) antenna can be used. Additionally, to ensure dual-band capability, an innovative E-shaped patch antenna can be used with a strategically placed shorting pin for miniaturization. The entire implant and interrogator system was rigorously optimized using an advanced in-house genetic algorithm, complemented by comprehensive simulations.

Figure 3:
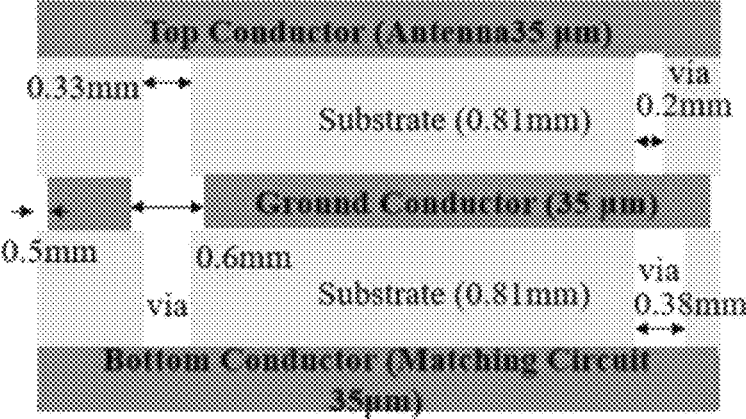
FIG. 3 shows a block diagram of a fabrication stack-up for a system, according to an embodiment of the subject invention.

FIG. 3 shows the innovative three-layer metallization structure implemented for the implanted and interrogator antennas. Each antenna features a radiating patch suitably positioned atop two substrate layers (which can each have a thickness of, for example 32 mils or about 32 mils). Also, the ground plane can be strategically situated within the middle metallization layer, and the matching and mixer circuits can be printed on the bottom layer. To facilitate seamless connectivity between these layers, high-precision via holes can be used.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (e.g., subranges within the disclosed range) and specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Figure 1B:
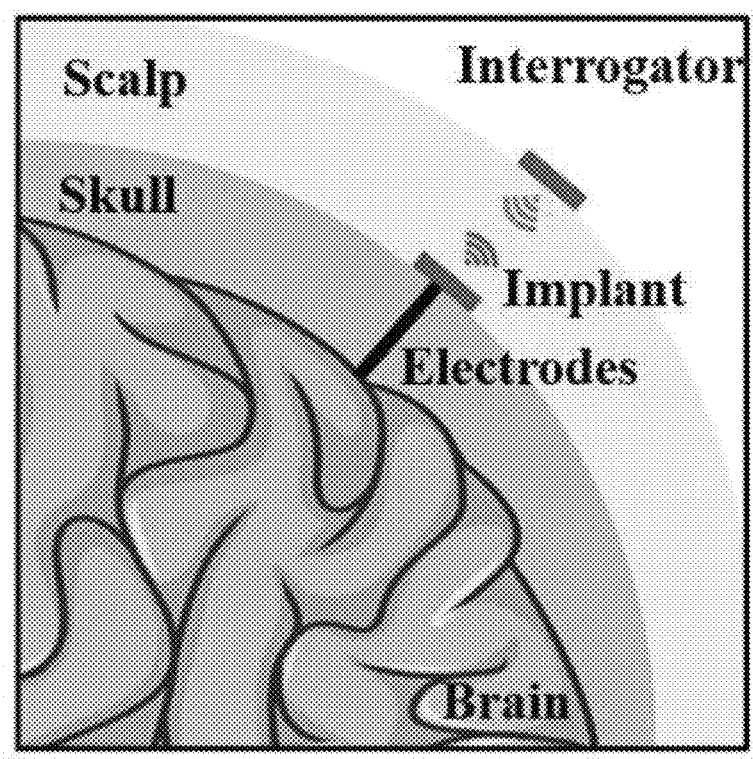
FIG. 1B shows a schematic view of a battery-less, wireless, multichannel implantable sensor implanted into a subject, according to an embodiment of the subject invention.
Figure 1C:
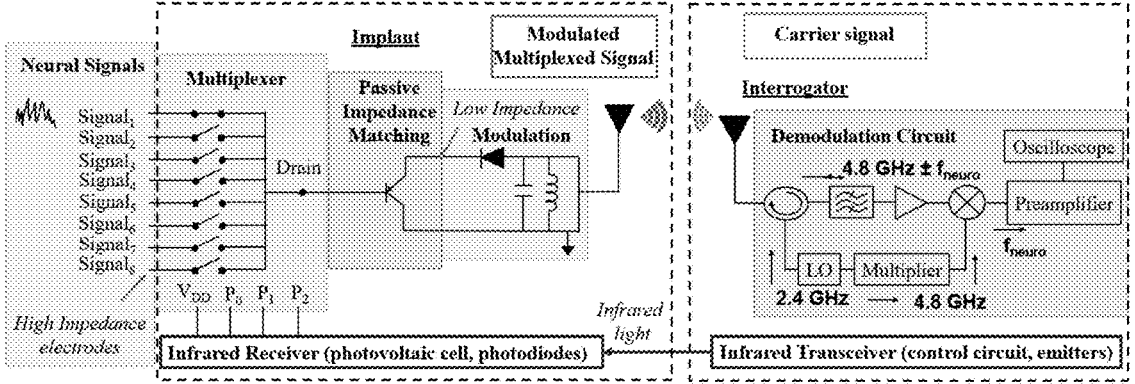
FIG. 1C shows a block diagram of a neurosensing system with passive impedance matching and a multiplexer, according to an embodiment of the subject invention.
Figure 1D:
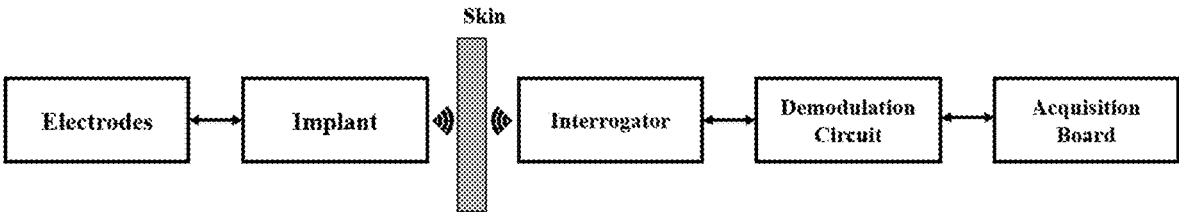
FIG. 1D shows a block diagram of components of a wireless neurosensing system, according to an embodiment of the subject invention.
Figure 2:
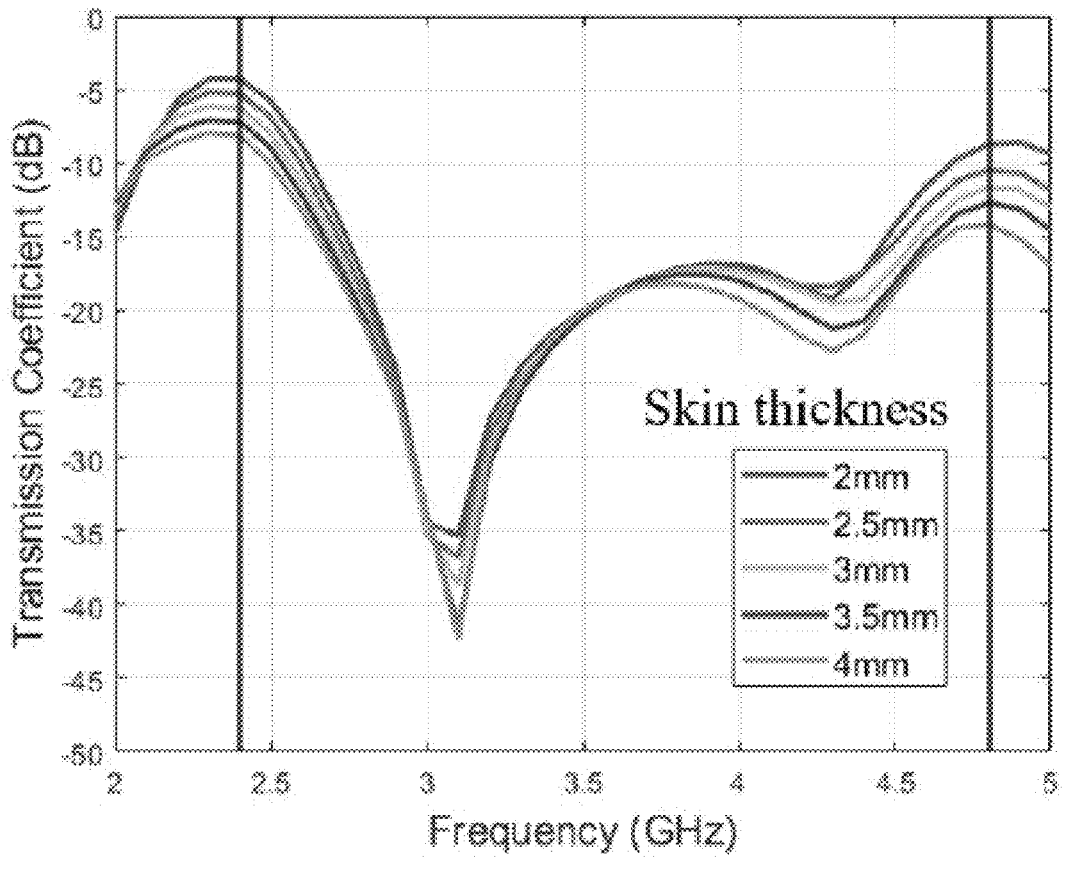
FIG. 2 shows a plot of transmission coefficient ($S_{21}$; in decibels (dB)) versus frequency (in gigahertz (GHz), showing the transmission coefficient between the transmitting and receiving antennas for different skin depths. The (blue) curve with the highest transmission coefficient value at 5 GHz is for a skin depth of 2 millimeters (mm); the (red) curve with the second-highest transmission coefficient value at 5 GHz is for a skin depth of 2.5 mm; the (yellow) curve with the third-highest transmission coefficient value at 5 GHz is for a skin depth of 3 mm; the (purple) curve with the second-lowest transmission coefficient value at 5 GHz is for a skin depth of 3.5 mm; and the (green) curve with the lowest transmission coefficient value at 5 GHz is for a skin depth of 4 mm.

A sensor system as disclosed herein and as depicted in FIGS. 1A-1C was tested with full wave simulations, which were employed using a skin model to emulate the electrical properties of the brain. A genetic algorithm was designed and used to optimize antenna performance for dual band operation at 2.4 gigahertz (GHz) ($\pm f_{neuro}$) and 4.8 GHz ($\pm f_{neuro}$), where $f_{neuro}$ is the neural signal frequency. In order to reduce antenna size, a shorting pin was incorporated in each antenna, leading to a 50% size reduction compared to related art designs. Antenna performance for different skin depths showed improvement over related art designs, as shown in FIG. 2 and the table in FIG. 5.

Example 2

A sensor system as disclosed herein and as depicted in FIGS. 1A-1C was fabricated. The fabrication stack-up is shown in FIG. 3. The implant and interrogator were fabricated using multilayers, leading to a 52% smaller footprint than in Chen et al. (Passive Impedance Matching for Implanted Brain-Electrode Interfaces, supra.). The implant was fabricated using 3D-printing comprising two layers of acrylate-based polymer ($\varepsilon_r$=2.8, tan δ=0.02) and three layers of silver conductive inks.

Figure 4:
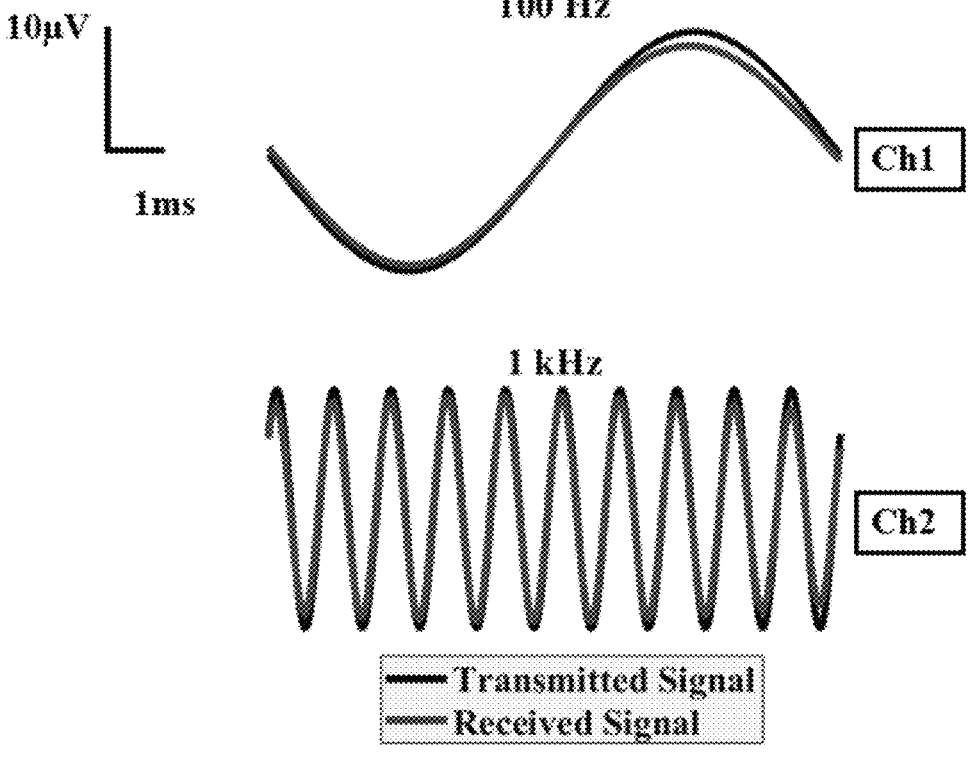
FIG. 4 shows plots of recovered sinusoidal signal for each channel. The top plot is for a frequency of 1 kilohertz (kHz), and the bottom plot is for a frequency of 500 Hertz (Hz).

Sinusoidal signals at frequencies of 100 Hertz (Hz) and 1 kHz were generated with constant amplitude at 20 microvolt peak to peak (μVpp) using channels 1 and 2, respectively. While switching the LED light sources to active channels 1 or 2, the signals corresponding to each channel were correctly recovered, as seen in FIG. 4.

Example 3

All animal procedures were approved and performed by the Institutional Animal Care and Use Committee (IACUC) at Florida International University (Approval No. 23-023). The animal was first acclimated for a period of one week prior to surgery and implantation. The surgery was done under complete anesthesia using ketamine 20 mg/kg and xylazine 2.0 mg/kg with butorphanol or Torbugesic 2 mg/kg BW. Anesthesia was maintained with continuous inhalation of 2% isoflurane/98% oxygen throughout the entire procedure. The implant component in the WiNS system was fully implanted under the pig's skin with the corresponding electrodes (complete skin closure). The procedure was done with sterile surgical components while the respiration and heart rate of the animal was monitored during the entire procedure. Also, the implant was placed in a pocket created under the skin near the top of the head of the animal. A craniotomy of approximately 2 cm in size was made to place the electrodes over the dura. The ECoG array (4 channels, but only 1 channel connected to the implant, FDA approved array) was placed on the cortex, targeting the brain region that detects somatosensation. In addition, a Ag/AgCl probe was fabricated for the ground implantation. The silver wire was electrochemically coated with chloride and was electrically connected to a screw in the skull.

After completing the surgery, the pig was placed on a heated blanket for recovery and monitored using a camera and/or in person in the animal facility until it was alert, responsive, and ambulatory. This occurred the same day. Also, the pig was visited for monitoring twice a day. After a period of one week, intracranial electric potentials were recorded using the WINS system under specified hind limb stimulation paradigm. The experimental paradigm was achieved with the pig fully anesthetized. The limbs excitation was done using small needle electrodes (gauge 26, 1 inch length) in the pig's hind limb to provide electrical pulses≤35 milliamps (mA). The pulse frequency was 2 Hz to 4.7 Hz with a negative pulse form of width 200 microseconds (μs) and 10 milliseconds (ms), using an isolated pulse stimulator (AM Systems Model 4200). Subsequently, the somatosensory event-related potentials (ERP) were recorded using the WiNS system. As noted, during the stimulation, the pig was sedated with intramuscular ketamine 20 mg/kg and xylazine 2.0 mg/kg intramuscular injection, or butorphanol (Torbugesic 2 mg/kg BW). At the same time, general anesthesia was maintained with continuous inhalation of 2% isoflurane/98% oxygen throughout the entire scanning procedure. The National Instruments (NI) USB-6259 system was used to continuously record the pig's sensory responses connected to the interrogator system. This approach eliminated use of an oscilloscope, replacing it with a laptop for continuous monitoring. In vivo measurements were performed approximately for a one month period after pig's implantation.

The recorded raw data were first filtered using a typical 60 Hz notch filter to suppress unwanted noise. Also, the datasets were band-pass filtered across 0.1 Hz to 100 Hz to target specific brain signals of interest. Each recording lasted two minutes and was segmented from –50 ms to 250 ms, referenced to the time of excitation. Somatosensory evoked potentials (SSEPs) were subsequently extracted by averaging the signal segments.

Figures 5, 6:
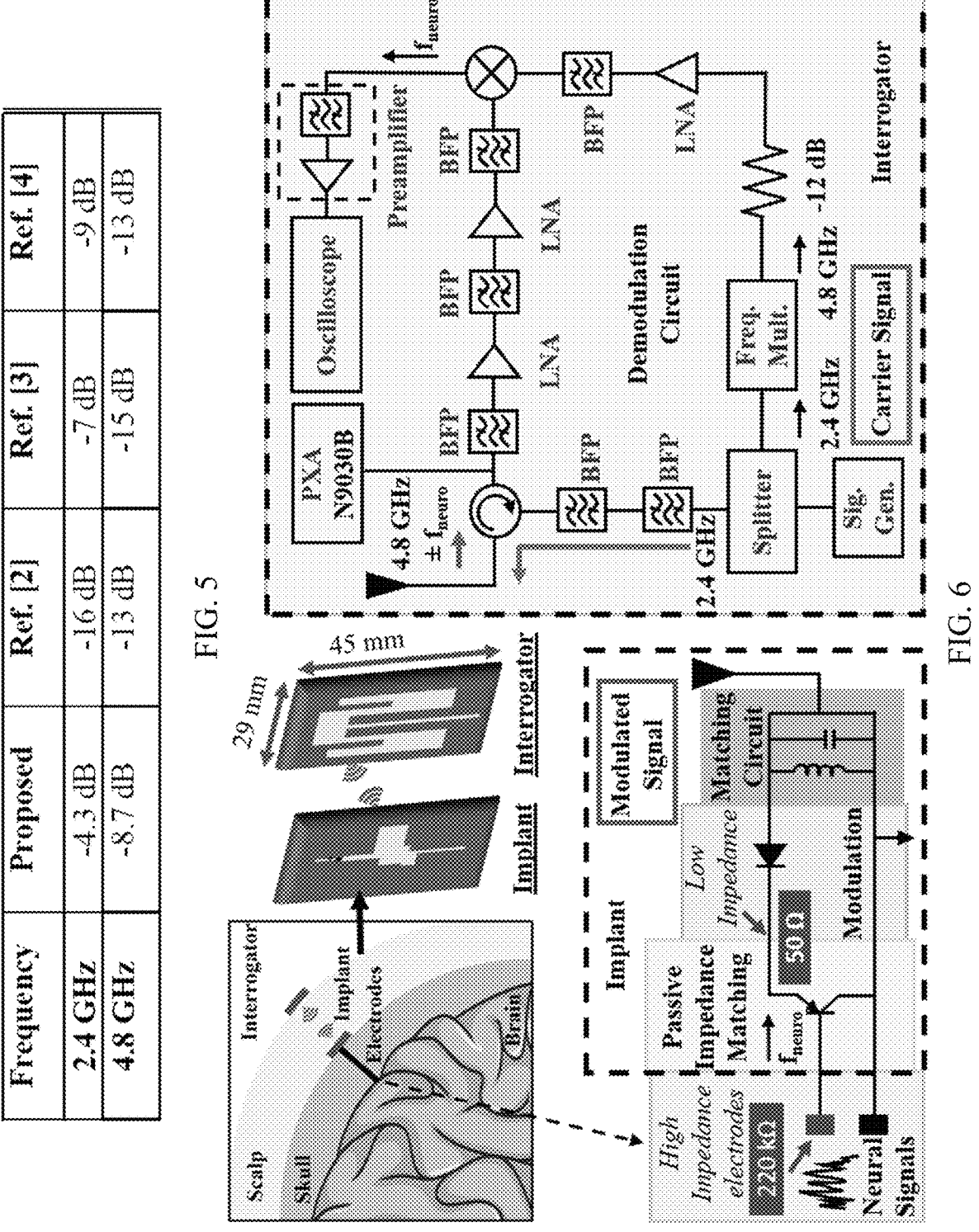
FIG. 5 shows a table of S21 comparison with related art systems at a skin depth of 2 mm. The column labeled "Proposed" is for a system according to an embodiment of the subject invention. The column labeled "Ref. [2]" is for a system as disclosed in Lee et al. (Miniaturized Fully Passive Brain Implant for Wireless Neuropotential Acquisition, IEEE Antennas Wirel. Propag. Lett., vol. 16, pp. 645-648, 2017; which is hereby incorporated by reference herein in its entirety). The column labeled "Ref. [3]" is for a system as disclosed in Chen et. al. (A Multi-Channel Passive Brain Implant for Wireless Neuropotential Monitoring, in IEEE Journal of Electromagnetics, RF and Microwaves in Medicine and Biology, vol. 2, no. 4, pp. 262-269, December 2018; which is hereby incorporated by reference herein in its entirety). The column labeled "Ref. [4]" is for a system as disclosed in Chen et. al. (Passive Impedance Matching for Implanted Brain-Electrode Interfaces, in IEEE Journal of Electromagnetics, RF and Microwaves in Medicine and Biology, vol. 3, no. 4, pp. 233-239, December 2019, doi: 10.1109/JERM.2019.2904024; which is hereby incorporated by reference herein in its entirety).
FIG. 6 shows a diagram of a wireless neurosensing system (WiNS), according to an embodiment of the subject invention. Though FIG. 6 lists certain dimensions, these are for exemplary purposes only and should not be construed as limiting.

Measurements were conducted to validate in vitro the recorder system presented in FIG. 6. Both skin phantom and pig skin were placed individually between the implanted recorder and interrogator antenna to emulate an implanted environment and the properties of skin (see FIGS. 8A-8D). A signal generator (Keysight/Agilent, N5182) provided a 2.4 GHz carrier of 10 dBm to the interrogator. An arbitrary function generator (Keysight 33600A) emulated neuropotentials as a sinusoidal waveforms (at frequency $f_{neuro}$). To generate less than 1 millivolt (mV) signals, a simple voltage divider circuit was used. First, the backscattered signal was captured in a PXA (Keysight N9030B, see the diagram in FIG. 9). The latter allows for reading backscattered power levels for different instances of frequency ($f_{neuro}$) and voltage (Vin) of the emulated neural signals as in FIG. 10A. Notably, the minimum detectable signal based on different electrodes impedance was tested as in FIG. 10B.

Figures 10C, 10D:
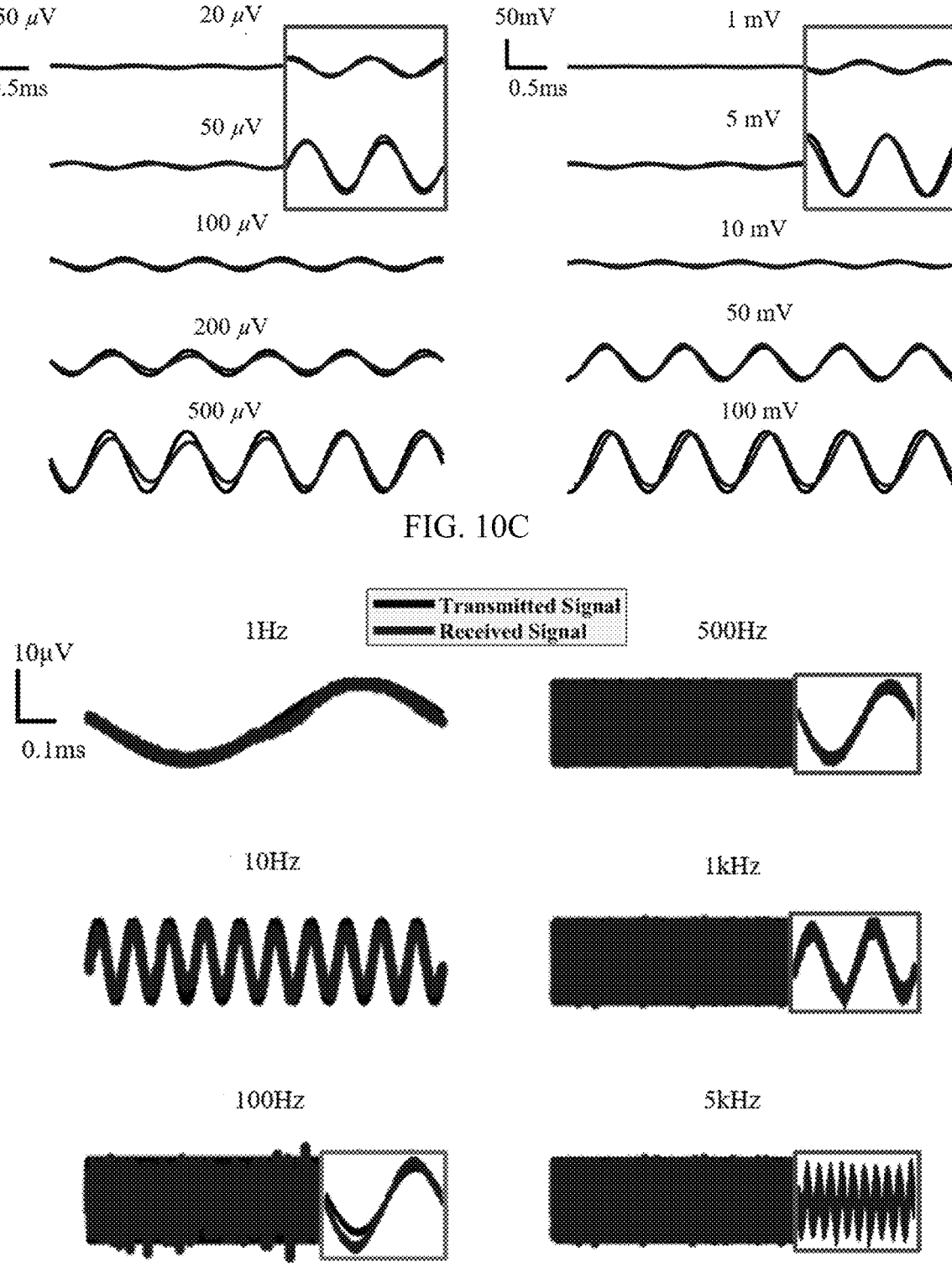
FIG. 10C shows signals varied in amplitude. The signal frequency was maintained constant at 1 kHz while the amplitude varied from 20 μV to 100 millivolts (mV). The left box shows a 2 millisecond (ms) segment at a 50 μVpp scale. The right box shows a 2 ms segment at a 10 millivolt peak to peak (mVpp) scale.
FIG. 10d shows signals varied in frequency. The signal amplitude was maintained constant at 20 μV while the frequency varied from 1 Hz to 5 kHz. The box near the bottom left shows a 10 ms segment on a 20 μVpp scale. The three boxes on the right show 2 ms segments each at a 20 μVpp scale.

To validate the recorder it was crucial to evaluate its ability to distinguish different frequency and amplitude. Therefore, emulated signals for our benchtop experiments were varied through different frequencies from 1 Hz to 5 kHz and amplitudes from 20 μV to 100 mV. To assess sensitivity due to changes in amplitude, sinusoidal signals were delivered to the implant with varying amplitude while keeping the frequency constant at 1 KHz. Notably, all neural signals were emulated using the signal generator Keysight (33600A). A voltage divider circuit was used to generate the <1 mV signals. The signals received at the interrogator were saved in an oscilloscope (Keysight, InfiniiVision DSOX 3034T) and then passed through a filter at 1 KHz for postprocessing in MATLAB as shown in FIG. 10C. To evaluate sensitivity due to frequency changes, the same setup was used. Also, to compare scenario with related art recorders, the electrode impedance was set to 33 kΩ via a resistor. Later, the received data from the oscilloscope was postprocessed in MATLAB as shown in FIG. 10D. This plainly showed that the recording system is capable of detecting low level neural signals. This was achieved by effectively reducing the losses of the system due to mismatches and poor coupling.

The somatosensory of evoked potentials (SSEPs) from swine were evaluated. By eliciting specific activity, a distinct time-locked waveform can be expected. The collected evoked potentials were averaged from several trials corresponding to neural somatosensory activation while exciting the hind limb of the animal as in FIGS. 11A-11C.

The raw data from the hindlimb stimulation were filtered using a 60 Hz notch filter and band-passed across 0.1 Hz to 100 Hz. Using the 2 Hz stimulation frequency for 2 minute recordings, approximately 240 trials were employed to obtain each SSEP. Each recording (2 min) was segmented from –50 ms to 250 ms and referenced to the time of stimulus onset. Subsequently, SSEPs were extracted by averaging across the signal segments. Comparison between the 1-channel SSEPs (FIG. 11A) and the control signal (FIG. 11C) was evaluated to demonstrate whether the implant can detect normal and evoked neural signals. Notably, control signals refer to the average of the recordings without stimulation. In addition, a comparison between the hind limb (HL)—contralateral (CL) stimulation (FIG. 11A) and HL ipsilateral (IL)—stimulation (FIG. 11B) were evaluated. As expected, the IL response is delayed in time and decreased in amplitude. Interictal spikes and epilepsy indicators have similar characteristics to those of evoked potentials. The latter demonstrated that the system is capable of recording epileptiform activity.

In addition, FIGS. 13A and 13B show a comparison between 8-channel SSEPs (FIG. 13A) and the control signal (FIG. 13B). The control signal refers to the average of the recordings with no stimulation.

The WiNS can reliably monitor the neuronal activity while fully implanted in a battery-free and wireless manner. This development is at least in part due to the new 3D additive manufactured system with 10-fold improvement over related art designs in MDS, and due to the packaging of the impedance matched circuit for complete implantation. A comparison with related art systems in terms of size, weight, channels, power consumption, MDS, communication distance, and experimental validation is provided in the table in FIG. 12. FIG. 14 also shows a comparison of the WiNS with related art systems. It can be seen that the WiNS can be an effective solution for monitoring epileptogenic foci in humans.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for sensing signals, the system comprising:
an implant configured to be embedded in a subject; and
an interrogator configured to communicate with the implant while being external to the subject,
the implant comprising:
    at least two electrodes; and
    a sensor connected to the at least two electrodes and comprising a transistor, a diode, and a first antenna configured to communicate with the interrogator while the implant is embedded in the subject,
the interrogator comprising a second antenna configured to communicate with the first antenna while the implant is embedded in the subject and the interrogator is external to the subject,
the interrogator being configured to generate a carrier signal, transmit the carrier signal to the implant, and receive a modulated signal from the implant,
the implant being configured to receive the carrier signal from the interrogator, mix the carrier signal with signals of interest (SoI) from the subject to generate the modulated signal, and backscatter the modulated signal to the interrogator, the implant and the interrogator not being connected to each other by any wire, the subject being a mammalian subject or an organoid, and the SoI comprising at least one of neural signals, cardiac signals, and electrochemically-based signals.

2. The system according to claim 1, further comprising a demodulation circuit connected to the interrogator and configured to demodulate the modulated signal.

3. The system according to claim 1, the transistor being a bipolar junction transistor (BJT), and the diode being a Schottky diode.

4. The system according to claim 1, the implant being coated with a biocompatible material.

5. The system according to claim 4, the biocompatible material being polydimethylsiloxane (PDMS).

6. The system according to claim 1, the first antenna and the second antenna each being a near-field communication (NFC) antenna.

7. The system according to claim 1, the first antenna comprising a shorting pin.

8. The system according to claim 1, the implant further comprising a passive impedance matching (PIM) network.

9. The system according to claim 1, the implant further comprising a photovoltaic (PV) cell and at least one photodiode (PD), and the interrogator further comprising a first light source configured to communication with the PV cell of the implant and at least one second light source configured to respectively communicate with the at least one PD of the implant.

10. A method for sensing signals, the method comprising:

implanting an implant into a skull of a subject;

generating, with an interrogator that is external to the subject, a carrier signal;

transmitting the carrier signal from the interrogator to the implant;

receiving, by the implant, the carrier signal from the interrogator;

mixing, by the implant, the carrier signal with signals of interest (SoI) from the subject to generate a modulated signal;

backscattering, by the implant, the modulated signal to the interrogator; and receiving, by the interrogator, the modulated signal from the implant the implant comprising:

at least two electrodes; and a sensor connected to the at least two electrodes and comprising a transistor, a diode, and a first antenna configured to communicate with the interrogator while the implant is embedded in the subject, the interrogator comprising a second antenna configured to communicate with the first antenna while the implant is embedded in the subject and the interrogator is external to the subject, the implant and the interrogator not being connected to each other by any wire, the subject being a mammalian subject or an organoid, and the SoI comprising at least one of neural signals, cardiac signals, and electrochemically-based signals.

11. The method according to claim 10, further comprising demodulating the modulated signal using a demodulation circuit connected to the interrogator.

12. The method according to claim 10, the transistor being a bipolar junction transistor (BJT), and the diode being a Schottky diode.

13. The method according to claim 10, further comprising, before implanting the implant into the skull of the subject, coating the implant with a biocompatible material.

14. The method according to claim 13, the biocompatible material being polydimethylsiloxane (PDMS).

15. The method according to claim 10, the first antenna and the second antenna each being a near-field communication (NFC) antenna.

16. The method according to claim 10, the first antenna comprising a shorting pin.

17. The method according to claim 10, the implant further comprising a passive impedance matching (PIM) network.

18. The method according to claim 10, the implant further comprising a photovoltaic (PV) cell and at least one photodiode (PD), the interrogator further comprising a first light source configured to communication with the PV cell of the implant and at least one second light source configured to respectively communicate with the at least one PD of the implant, and the method further comprising:

communicating, by the first light source, with the PV cell of the implant; and using the at least one second light source to respectively trigger the at least one PD of the implant.

19. A system for sensing signals, the system comprising:

an implant configured to be embedded in a subject; and an interrogator configured to communicate with the implant while being external to the subject, the implant comprising:

at least two electrodes; and a sensor connected to the at least two electrodes and comprising a transistor, a diode, and a first antenna configured to communicate with the interrogator while the implant is embedded in the subject, the interrogator comprising a second antenna configured to communicate with the first antenna while the implant is embedded in the subject and the interrogator is external to the subject, the interrogator being configured to generate a carrier signal, transmit the carrier signal to the implant, and receive a modulated signal from the implant, the implant being configured to receive the carrier signal from the interrogator, mix the carrier signal with signals of interest (SoI) from the subject to generate the modulated signal, and backscatter the modulated signal to the interrogator, the implant and the interrogator not being connected to each other by any wire, the system further comprising a demodulation circuit connected to the interrogator and configured to demodulate the modulated signal, the transistor being a bipolar junction transistor (BJT), the diode being a Schottky diode, the implant being coated with a biocompatible material, the first antenna and the second antenna each being a near-field communication (NFC) antenna, the first antenna comprising a shorting pin, the implant further comprising a passive impedance matching (PIM) network, the subject being a mammalian subject or an organoid, and the SoI comprising at least one of neural signals, cardiac signals, and electrochemically-based signals.

19

20

20. The system according to claim 19, the implant further comprising a photovoltaic (PV) cell and at least one photodiode (PD), the interrogator further comprising a first light source configured to communication with the PV cell of the implant and at least one second light source configured to respectively communicate with the at least one PD of the implant, and the biocompatible material being polydimethylsiloxane (PDMS).

\* \* \* \* \*